United States Patent [19]
Hillman et al.

[11] Patent Number: 6,001,620
[45] Date of Patent: Dec. 14, 1999

[54] HUMAN LYSOPHOSPHATIDIC ACID ACYLTRANSFERASE

[75] Inventors: Jennifer L. Hillman, Mountain View; Henry Yue, Sunnyvale; Karl J. Guegler, Menlo Park; Neil C. Corley, Mountain View, all of Calif.

[73] Assignee: Incyte Pharmaceuticals, Inc., Palo Alto, Calif.

[21] Appl. No.: 09/259,706

[22] Filed: Mar. 1, 1999

Related U.S. Application Data

[62] Division of application No. 09/030,652, Feb. 25, 1998, Pat. No. 5,888,793.

[51] Int. Cl.$^6$ .................................................... C12N 9/10
[52] U.S. Cl. ........................................................ 435/193
[58] Field of Search ............................................. 435/193

[56] References Cited

U.S. PATENT DOCUMENTS 5,563,058  10/1996  Davies et al. ............................ 435/193

OTHER PUBLICATIONS

Morand et al., Biophys. Res. Commun., 1998, vol. 244(1), pp. 79–84, 1998.
Eberhardt et al., Journal of Biological Chemistry, 1997, vol. 272(32), pp. 20299–20305, Aug. 1997.
Moolenaar, W.H., "Lysophosphatidic Acids, a Multifunctional Phospholipid Messenger", *J. Biol. Chem.*, 270: 12949–12952 (1995).
Xu, Y. et al., "Lysophospholipids activate ovarian and breast cancer cells", *Biochem J.*, 309: 933–940 (1995).
Imamura, F. et al., "Induction of in Vitro Tumor Cell Invasion of Cellular Monolayers by Lysophosphatidic Acid or Phospholipase D", *Biochem. Biophys. Res Comm.*, 193: 497–503 (1993).
Bursten, S.L. et al., "Lipid A activation of glomerular mesangial cells: mimicry of the bioactive lipid, phospatidic acid", *Am. J. Physiol*, 262: C328–C338 (1992).
Bursten, S.L. et al., "Interleukin–1 Rapidly Stimulates Lysophosphatidate A cyltransferase and Phosphatidate Phosphohydrolaase Acititivites in Human Mesangial Cells", *J. Biol. Chem.*, 266: 20732–20743 (1991).
Kester, M., "Platelet–Activating Factor Stimulates Phospatidic Acid Formation in Cultured Rat Mesangial Cells: Rolls of Phopholipase D, Diglyceride Kinase, and De Novo Phopholipid Synthesis", *J. Cell. Physiol.*, 156: 317–325 (1993).
Abraham, E. et al., "Phosphatidic Acid Signaling Mediates Lung Cytokine Expression and Lung Inflammatory Injury After Hemorrhage in Mice", *J. Exp. Med.*, 181: 569–575 (1995).
Rice, G. et al., "Protection from endotoxic shock in mice by pharmacologic inhibition of phosphatidic acid", *Proc. Natl. Acad. Sci. USA*, 91: 3857–3861 (1994).
Stamps, M. et al., (Direct Submission), GenBank Sequence Database (Accession AF015811), National Center for Biotechnology Information, National Library of Medicine, Bethesda, Maryland, 20894, (GI 2317724; GI 2317725) No Date Provided.
Stamps et al., GenBank Accession AF015811 "Mus musculus putative lysophosphatidic acid acyltransferase mRNA, complete Cds", Aug. 7, 1997.
Kume, K. et al., "cDNA cloning and expression of murine 1–acyl–sn–glycerol–3–phosphate acyltransferase", *Biochem. Biophys. Res. Commun.* 237(3): 663–666 (1997).
Coleman, J., "Characterization of the *Escherichia coli* gene for 1–acyl–sn–glycerol–3–phosphate acyltransferase (plsC)", *Mol. Gen. Genet.* 232(2): 295–303 (1992).
Miki, Y. et al., "Acyl–acceptor specificities of 1–acylglycerolphosphate acyltransferase and 1–acylglycerophosphorylcholine acyltransferase resolved from rat linermicrosomes", *Eur. J. Biochem.* 81(3): 433–441 (1977).
Yamashita, S. et al., "Separation of 1–acylglycerolphosphate acyltransferase and 1–acylglycerolphosphorylcholine acyltransferase of rat liver microsomes", *Proc. Natl. Acad. Sci. USA* 72(2): 600–603 (1975).

*Primary Examiner*—Ponnathapu Achutamurthy
*Assistant Examiner*—Bradley S. Mayhew
*Attorney, Agent, or Firm*—Colette C. Muenzen; Incyte Pharmaceuticals, Inc.

[57] ABSTRACT

The invention provides a human lysophosphatidic acid acyltranferase (HLPAAT) and polynucleotides which identify and encode HLPAAT. The invention also provides expression vectors, host cells, antibodies, agonists, and antagonists. The invention also provides methods for treating or preventing disorders associated with expression of HLPAAT.

2 Claims, 10 Drawing Sheets

FIGURE 1A

```
         10              19              28              37              46              55
5'C  CCA CGC GTC     CGG CGG TCG     CCG CGG GAT     TTG GAG CTG     CCT AGC CTC     GCG GTC GCT 64              73              82              91             100             109
     TTG GCA GCA     TGT AAG CAG     CTG TTT GCC     AAG AAC CCA     GGT CAC TGC     TAA GAA AGG 118             127             136             145             154             163
     GTG CCT TCG     GGA GAA GAG     TGT CCA GAG     GAT ACC AAT     GCC AGA TGC     ATC TGG AGT 172             181             190             199             208             217
     TAC ACT CAG     CAC TCG CAG     TAT GAG ACA     TTG TGT GCC     AGC ATC TCT     TTC CTT CTG 226             235             244             253             262             271
     GCA AAG ACT     GTA GCT CTC     CAG GTA GGA     GGA TCC TGG     AAG CTG TGA     GCA CCA GGA 280             289             298             307             316             325
     GCC TTG CCA     GAG GAG GAT     GGG GCC AGA     TAT GAA CTC     TCT ACC ATG     AAC ATG GTT 334             343             352             361             370             379
     CTC GGC TTA     TGA AGG AAT     TTT AAG AAC     AGT TAT GAA     ATT TCC ACA     TAT TCA 388             397             406             415             424             433
     AGT CAA AAG     CCT TCT GTG     TGA AGT GCC     AGT GAT TAC     CCC TCC ACA     GGA GTT ATC 442             451             460             469             478             487
     AGG ATT TTT     CTG GCA CCA     AGT TTA ATT     CTT CTT CGT     ACT TCT GGT     AGT GAC AGA
```

```
            496     505     514     523     532     541
TCT GCA GGG CAG ATT TAT CTG TTG AAT GCT CTT GGG CAG GAA AAC CAT GTA AAA
            550     559     568     577     586     595
CCT CTG GAA GCA GCA TCA GGA CAG AGC AGA GCC CCC GTC CTC ACT GCT CAC
            604     613     622     631     640     649
TTG CAC AGA AAC TCC ATC TGG ACT CGG ATG CTT TTA CTG AAG ACC CAT CTA GCT
            658     667     676     685     694     703
TCA ATC TTT AGA GTC CAT CCA TTC TGG AGA GAC CTG GCG TTT GCA GTT GCC
            712     721     730     739     748     757
TCC TGT CGT GTT TTT CTG TCA TTC TGT TCC CAG GCC TTC TAT TCA GGC GGT
            766     775     784     793     802     811
TGA AGG GTG TGG ACT TTG GAA TGG GGT TTG CTG TTC TTC GGG AAC TTG CTT CCT
            820     829     838     847     856     865
TTC CCT GGC TGG TGT CAG GAA CCA TCT GAA GGC TGC AAT TTG TTC TTA
            874     883     892     901     910     919
GGG AGG CAG GTG CTG GCC TGG CCT GGA TCT TCC ACC ATG TTC CTG TTG CTG CCT
            928     937     946     955     964     973
TTT GAT AGC CTG ATT GTC AAC CTT CTG GGC ATC TCC CTG ACT GTC CTC TTC ACC
```

FIGURE 1B

```
       982         991        1000       1009       1018       1027
CTC CTT CTC GTT TTC ATC ATA GTG CCA GCC ATT TTT GGA GTC TCC TTT GGT ATC 1036        1045       1054       1063       1072       1081
CGC AAA CTC TAC ATG AAA AGT CTG TTA AAA ATC TTT GCG TGG GCT ACC TTG AGA 1090        1099       1108       1117       1126       1135
ATG GAG CGA GGA GCC AAG GAG AAG AAC CAC CAG CTT TAC AAG CCC TAC ACC AAC 1144        1153       1162       1171       1180       1189
GGA ATC ATT GCA AAG GAT CCC ACT TCA CTA GAA GAG ATC AAA GAG ATT CGT 1198        1207       1216       1225       1234       1243
CGA AGT GGT AGT AAG GCT CTG GAC AAC ACT CCA GAG TTC GAG CTC TCT GAC 1252        1261       1270       1279       1288       1297
ATT TTC TAC TTT TGC CGG AAA GGA ATG GAG ACC ATT ATG GAT GAT GAG GTG ACA
                                  M   E   T   I   M   D   D   E   V   T 1306        1315       1324       1333       1342       1351
AAG AGA TTC TCA GCA GAA GAA CTG GAG TCC TGG AAC CTG CTG AGC AGA ACC AAT
 K   R   F   S   A   E   E   L   E   S   W   N   L   L   S   R   T   N 1360        1369       1378       1387       1396       1405
TAT AAC TTC CAG TAC ATC AGC CTT CGG CTC ACG GTC CTG TGG GGG TTA GGA GTG
 Y   N   F   Q   Y   I   S   L   R   L   T   V   L   W   G   L   G   V
```

FIGURE 1C

```
                                1414                    1423                    1432                    1441                    1450                    1459
                                CTG ATT CGG TAC TGC TTT CTG CTG CCG CTC AGG ATA GCA CTG GCT TTC ACA GGG
                                 L   I   R   Y   C   F   L   L   P   L   R   I   A   L   A   F   T   G 1468                    1477                    1486                    1495                    1504                    1513
                                ATT AGC CTT CTG GTG GTG GGC ACA ACT GTG GTG GGA TAC TTG CCA AAT GGG AGG
                                 I   S   L   L   V   V   G   T   T   V   V   G   Y   L   P   N   G   R 1522                    1531                    1540                    1549                    1558                    1567
                                TTT AAG GAG TTC ATG AGT AAA CAT GTT CAC TTA ATG TGT TAC CGG ATC TGC GTG
                                 F   K   E   F   M   S   K   H   V   H   L   M   C   Y   R   I   C   V 1576                    1585                    1594                    1603                    1612                    1621
                                CGA GCG CTG ACA GCC ATC ATC ACC TAC CAT GAC AGG GAA AAC AGA CCA AGA AAT
                                 R   A   L   T   A   I   I   T   Y   H   D   R   E   N   R   P   R   N 1630                    1639                    1648                    1657                    1666                    1675
                                GGT GGC ATC TGT GTG GCC AAT CAT ACC TCA CCG ATC GAT GTG ATC ATC TTG GCC
                                 G   G   I   C   V   A   N   H   T   S   P   I   D   V   I   I   L   A 1684                    1693                    1702                    1711                    1720                    1729
                                AGC GAT GGC TAT TAT GCC ATG GTG GGT CAA GTG CAC GGG GGA CTC ATG GGT GTG
                                 S   D   G   Y   Y   A   M   V   G   Q   V   H   G   G   L   M   G   V 1738                    1747                    1756                    1765                    1774                    1783
                                ATT CAG AGA GCC ATG GTG AAG GCC TGC CCA CAC GTC TGG TTT GAG CGC TCG GAA
                                 I   Q   R   A   M   V   K   A   C   P   H   V   W   F   E   R   S   E
```

FIGURE 1D

```
            1792            1801            1810            1819            1828            1837
         GTG AAG GAT CGC CAC CTG GTG GCT CTG AAG AGA CTG ACT GAA CAT GTG CAA GAT AAA
          V   K   D   R   H   L   V   A   L   K   R   L   T   E   H   V   Q   D   K 1846            1855            1864            1873            1882            1891
         AGC AAG CTG CCT ATC CTC ATC TTC CCA GAA GGA ACC TGC ATC AAT AAT ACA TCG
          S   K   L   P   I   L   I   F   P   E   G   T   C   I   N   N   T   S 1900            1909            1918            1927            1936            1945
         GTG ATG ATG TTC AAA AAG GGA AGT TTT GAA ATT GGA GCC ACA GTT TAC CCT GTT
          V   M   M   F   K   K   G   S   F   E   I   G   A   T   V   Y   P   V 1954            1963            1972            1981            1990            1999
         GCT ATC AAG TAT GAC CCT CAA TTT GGC GAT GCC TTC TGG AAC AGC AGC AAA TAC
          A   I   K   Y   D   P   Q   F   G   D   A   F   W   N   S   S   K   Y 2008            2017            2026            2035            2044            2053
         GGG ATG GTG ACG TAC CTG CTG CGA ATG ATG ACC AGC TGG GCC ATT GTC TGC AGC
          G   M   V   T   Y   L   L   R   M   M   T   S   W   A   I   V   C   S 2062            2071            2080            2089            2098            2107
         GTG TGG TAC CTG CCT CCC ATG ACT AGA GAG GCA GAT GAA GCA GCT GTC CAG TTT
          V   W   Y   L   P   P   M   T   R   E   A   D   E   A   A   V   Q   F 2116            2125            2134            2143            2152            2161
         GCG AAT AGG GTG AAA TCT GCC ATT GCC AGG CAG GGA GGA CTT GTG GAC CTG CTG
          A   N   R   V   K   S   A   I   A   R   Q   G   G   L   V   D   L   L
```

FIGURE 1E

```
              2170              2179              2188              2197              2206              2215
          TGG GAT GGG GGC CTG AAG AGG GAG AAG GTG AAG GAC ACG TTC AAG GAG GAG CAG
           W   D   G   G   L   K   R   E   K   V   K   D   T   F   K   E   E   Q
              2224              2233              2242              2251              2260              2269
          CAG AAG CTG TAC AGC AAG ATG ATC GTG GGG AAC CAC AAG GAC AGG AGC CGC TCC
           Q   K   L   Y   S   K   M   I   V   G   N   H   K   D   R   S   R   S
              2278              2287              2296              2305              2314              2323
          TGA GCC TGC CTC CAG CTG GCT GGG CCC ACC GTG CGG GGT GCC AAC GGG CTC AGA
              2332              2341              2350              2359              2368              2377
          GCT GGA GTT GCC GCC GCC CCC ACT GCT GTG TCC TTT CCA GAC TCC AGG GCT
              2386              2395              2404              2413              2422              2431
          CCC CGG GCT GCT CTG GAT CCC AGG ACT CCG GCT TTC GCC GAG CCG CAG CGG GAT
              2440              2449              2458              2467              2476              2485
          CCC TGT GCA CCC GGC GCA GCT ACC CTT GGT GGT CTA AAC GGA TGC TGC TGG GTG
              2494              2503              2512              2521              2530              2539
          TTG CGA CCC AGG ACG AGA TGC CTT GTT TCT TTT ACA ATA AGT CGT TGG AGG AAT
              2548              2557              2566              2575              2584              2593
          GCC ATT AAA GTG AAC TCC CCA CCT TTG CAC GCT GTG CGG GCT GAG TGG TTG GGG
```

FIGURE 1F

```
          2602        2611        2620        2629        2638        2647
AGA TGT GGC CAT GGT CTT GTG CTA GAG ATG GCG GTA CAA GAG TCT GTT ATG CAA 2656        2665        2674        2683        2692        2701
GCC CGT GTG CCA GGG ATG TGC TGG GGG CGG CCA CCC GCT CTC CAG GAA AGG CAC 2710        2719        2728        2737        2746        2755
AGC TGA GGC ACT GTG GCT GGC TTC GGC CTC AAC ATC GCC CCC AGC CTT GGA GCT 2764        2773        2782        2791        2800        2809
CTG CAG ACA TGA TAG GAA AAC TGT CAT CTG CAG GGG CTT TCA GCA AAA TGA 2818        2827        2836        2845        2854        2863
AGG GTT AGA TTT TTA TGC TGC TGA TGG GGT TAC TAA AGG GAG GGG AAG AGG 2872        2881        2890        2899        2908        2917
CCA GGT GGG CCG CTG ACT GGG CCA TGG GGA GAA CGT GTG TTC GTA CTC CAG GCT 2926        2935        2944        2953        2962        2971
AAC CCT GAA CTC CCC ATG TGA TGC GCG CTT TGT TGA ATG TGT GTC TCG GTT TCC 2980        2989        2998        3007        3016        3025
CCA TCT GTA ATA TGA GTC GGG AAT GGT GGT GAT TCC TAC CTC ACA GGG CTG 3034        3043        3052        3061        3070        3079
TTG TGG GGA TTA AAG TGC TGC GGG TGA GTG AAG GAC ACA TCA CGT TCA GTG TTT
```

FIGURE 1G

```
     3088      3097      3106      3115      3124      3133
CAA GTA CAG GCC CAC AAA ACG GGG CAC GGC AGG CCT GAG CTC AGA GCT GCT GCA 3142      3151      3160      3169      3178      3187
CTG GGC TTT GGA TTT GTT CTT GTG AGT AAA TAA AAC TGG CTG GTG AAT GAA AAA

AAA AA 3'
```

HUMAN LYSOPHOSPHATIDIC ACID ACYLTRANSFERASE

This application is a divisional application of U.S. application Ser. No. 09/030,652, filed Feb. 25, 1998, now U.S. Pat. No. 5,888,793.

FIELD OF THE INVENTION

This invention relates to nucleic acid and amino acid sequences of a human lysophosphatidic acid acyltransferase and to the use of these sequences in the diagnosis, treatment, and prevention of cancer and autoimmune disorders.

BACKGROUND OF THE INVENTION

Lysophosphatidic acid acyltransferase (LPAAT) catalyzes the acylation of lysophosphatidic acid (LPA) to phosphatidic acid. LPA is the simplest glycerophospholipid, consisting of a glycerol molecule, a phosphate group, and a monosaturated fatty acyl chain. LPAAT adds a second fatty acyl chain to LPA, producing phosphatidic acid (PA). PA is the precursor molecule for diacylglycerols, which are necessary for the production of phospholipids, and for triacylglycerols, which are essential biological fuel molecules.

In addition to being a crucial precursor molecule in biosynthetic reactions, LPA has recently been added to the list of intercellular lipid messenger molecules. LPA interacts with G protein-coupled receptors, coupling to various independent effector pathways including inhibition of adenylate cyclase, stimulation of phospholipase C, activation of MAP kinases, and activation of the small GTP-binding proteins Ras and Rho. (Moolenaar, W. H. (1995) J. Biol. Chem 28-:12949–12952.) The physiological effects of LPA have not been fully characterized yet, but they include promoting growth and invasion of tumor cells. Addition of LPA to ovarian or breast cancer cell lines induced cell proliferation, increased intracellular calcium levels, and activated MAP kinase. (Xu, Y et al. (1995) Biochem. J. 309:933–940.) In addition, LPA induced MM1 tumor cells to invade cultured mesothelial cell monolayers. (Imamura, F. et al. (1993) Biochem. Biophys. Res. Comm. 193:497–503.)

Phosphatidic acid (PA), the product of LPAAT, is also a messenger molecule. PA is a key messenger in a common signaling pathway activated by proinflammatory mediators such as interleukin-1β, tumor necrosis factor α, platelet activating factor, and lipid A. (Bursten, S. L. et al. (1992) Am. J. Physiol. 262:C328–C338; Bursten S. L. et al. (1991) J. Biol. Chem. 255:20732–20743; Kester, M. (1993) J. Cell Physiol. 156:317–325.) For example, in a mouse model of inflammatory response, inhibition of LPAAT reduced lipopolysaccharide-mediated endotoxic shock. (Abraham, E. et al. (1995) J. Exp. Med. 181:569–575; Rice, G. C. et al. (1994) Proc. Natl. Acad. Sci. USA 91:3857–3861.) Thus, LPAAT activity may mediate inflammatory responses to various proinflammatory agents.

The discovery of a new human lysophosphatidic acid acyltranferase and the polynucleotides encoding it satisfies a need in the art by providing new compositions which are useful in the diagnosis, treatment, and prevention of cancer and autoimmune disorders.

SUMMARY OF THE INVENTION

The invention is based on the discovery of a new human lysophosphatidic acid acyltransferase (HLPAAT), the polynucleotides encoding HLPAAT, and the use of these compositions for the diagnosis, treatment, or prevention of cancer and autoimmune disorders.

The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 90% polynucleotide sequence identity to the polynucleotide encoding the polypeptide comprising the amino acid sequence of SEQ ID NO:1 or a fragment of SEQ ID NO:1.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 90% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing an autoimmune disorder, the method comprising administering to a subject in need of such treatment an effective amount of an antagonist of the polypeptide having the amino acid sequence of SEQ ID NO:1 or a fragment of SEQ ID NO:1.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, 1F, 1G, and 1H show the amino acid sequence (SEQ ID NO:1) and nucleic acid sequence (SEQ ID NO:2) of HLPAAT. The alignment was produced using ACDNASIS PRO software (Hitachi Software Engineering Co. Ltd., San Bruno, Calif.).

FIGS. 2A and 2B show the amino acid sequence alignments between HLPAAT (Incyte Clone number 2057904; SEQ ID NO:1), and mouse lysophosphatidic acid acyltransferase (mLPAAT) (GI2317725; SEQ ID NO:3), produced using the multisequence alignment program of LASERGENE software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HLPAAT," as used herein, refers to the amino acid sequences of substantially purified HLPAAT obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HLPAAT, increases or prolongs the duration of the effect of HLPAAT. Agonists may include proteins, nucleic acids, carbohydrates, or any other molecules which bind to and modulate the effect of HLPAAT.

An "allele" or an "allelic sequence," as these terms are used herein, is an alternative form of the gene encoding HLPAAT. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence. "Altered" nucleic acid sequences encoding HLPAAT, as described herein, include those sequences with deletions, insertions, or substitutions of different nucleotides, resulting in a polynucleotide the same HLPAAT or a polypeptide with at least one functional characteristic of HLPAAT. Included within this definition are polymorphisms which may or may not be readily detectable using a particular oligonucleotide probe of the polynucleotide encoding HLPAAT, and improper or unexpected hybridization to alleles, with a locus other than the normal chromosomal locus for the polynucleotide sequence encoding HLPAAT. The encoded protein may also be "altered," and may contain deletions, insertions, or substitutions of amino acid residues which produce a silent change and result in a functionally equivalent HLPAAT. Deliberate amino acid substitutions may be made on the basis of similarity in polarity, charge, solubility, hydrophobicity, hydrophilicity, and/or the amphipathic nature of the residues, as long as the biological or immunological activity of HLPAAT is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HLPAAT which are preferably about 5 to about 15 amino acids in length and which retain some biological activity or immunological activity of HLPAAT. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule. "Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to HLPAAT, decreases the amount or the duration of the effect of the biological or immunological activity of HLPAAT. Antagonists may include proteins, nucleic acids, carbohydrates, antibodies, or any other molecules which decrease the effect of HLPAAT.

As used herein, the term "antibody" refers to intact molecules as well as to fragments thereof, such as Fa, F(ab')$_2$, and Fv fragments, which are capable of binding the epitopic determinant. Antibodies that bind HLPAAT polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HLPAAT, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HLPAAT or fragments of HLPAAT may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

"Consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW Fragment Assembly system (GCG, Madison, WIS.). Some sequences have been both extended and assembled to produce the consensus sequence.

As used herein, the term "correlates with expression of a polynucleotide" indicates that the detection of the presence of nucleic acids, the same or related to a nucleic acid sequence encoding HLPAAT, by northern analysis is indicative of the presence of nucleic acids encoding HLPAAT in a sample, and thereby correlates with expression of the transcript from the polynucleotide encoding HLPAAT.

A "deletion," as the term is used herein, refers to a change in the amino acid or nucleotide sequence that results in the absence of one or more amino acid residues or nucleotides.

The term "derivative," as used herein, refers to the chemical modification of HLPAAT, of a polynucleotide sequence encoding HLPAAT, or of a polynucleotide sequence complementary to a polynucleotide sequence encoding HLPAAT. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.) The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of HLPAAT. For example, modulation may cause an increase or a decrease in protein activity, binding characteristics, or any other biological, functional, or immunological properties of HLPAAT.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the encoded polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HLPAAT, or fragments thereof, or HLPAAT itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HLPAAT, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

The Invention

The invention is based on the discovery of a new human lysophosphatidic acid acyltransferase (HLPAAT), the polynucleotides encoding HLPAAT, and the use of these compositions for the diagnosis, treatment, or prevention of cancer and autoimmune disorders.

Nucleic acids encoding the HLPAAT of the present invention were first identified in Incyte Clone 2057904 from the bronchial epithelium cDNA library (BEPINOT01) using a computer search for amino acid sequence alignments. A consensus sequence, SEQ ID NO:2, was derived from the following overlapping and/or extended nucleic acid sequences: Incyte Clones 2057904 (BEPINOT01), 1731129 (BRSTTUT08), 2379885 (ISLTNOT01), 1911576 (CONNTUT01), 1573592 (LNODNOT03), 143129 (TLYMNOR01), and 1664960 (BRSTNOT09).

In one embodiment, the invention encompasses a polypeptide comprising the amino acid sequence of SEQ ID NO:1, as shown in FIGS. 1A, 1B, 1C, 1D, 1E, 1F, 1G, and 1H. HLPAAT is 334 amino acids in length and has four potential glycosylation sites at residues $N_{125}$, $N_{205}$, $N_{206}$, and $N_{240}$. HLPAAT also has three potential cAMP- and cGMP-dependent protein kinase phosphorylation sites at residues $S_{11}$, $T_{181}$, and $S_{213}$, five potential casein kinase II phosphorylation sites at residues $T_3$, $S_{14}$, $T_{108}$, $S_{128}$, and $T_{311}$, and four potential protein kinase C phosphorylation sites at residues $T_{10}$, $S_{35}$, $S_{241}$, and $T_{311}$. As shown in FIGS. 2A and 2B, HLPAAT has chemical and structural homology with mouse mLPAAT (GI 2317725; SEQ ID NO:3). In particular, HLPAAT and mLPAAT share 85% identity, as well as sharing several potential glycosylation and phosphorylation sites. The fragment of SEQ ID NO:2 from about nucleotide 2210 to about nucleotide 2270 is useful as a hybridization probe. Northern analysis shows the expression of this sequence in various libraries, at least 51% of which are immortalized or cancerous and at least 28% of which involve immune response. Of particular note is the expression of HLPAAT in libraries from cancerous reproductive and gastrointestinal tissues.

The invention also encompasses HLPAAT variants. A preferred HLPAAT variant is one which has at least about 80%, more preferably at least about 90%, and most preferably at least about 95% amino acid sequence identity to the HLPAAT amino acid sequence, and which contains at least one functional or structural characteristic of HLPAAT.

The invention also encompasses polynucleotides which encode HLPAAT. In a particular embodiment, the invention encompasses a polynucleotide sequence comprising the sequence of SEQ ID NO:2, which encodes an HLPAAT.

The invention also encompasses a variant of a polynucleotide sequence encoding HLPAAT. In particular, such a variant polynucleotide sequence will have at least about 80%, more preferably at least about 90%, and most preferably at least about 95% polynucleotide sequence identity to the polynucleotide sequence encoding HLPAAT. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of HLPAAT.

It will be appreciated by those skilled in the art that as a result of the degeneracy of the genetic code, a multitude of polynucleotide sequences encoding HLPAAT, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HLPAAT, and all such variations are to be considered as being specifically disclosed.

Although nucleotide sequences which encode HLPAAT and its variants are preferably capable of hybridizing to the nucleotide sequence of the naturally occurring HLPAAT under appropriately selected conditions of stringency, it may be advantageous to produce nucleotide sequences encoding HLPAAT or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HLPAAT and its derivatives without altering the encoded amino acid sequences include the production of RNA transcripts having more desirable properties, such as a greater half-life, than transcripts produced from the naturally occurring sequence.

The invention also encompasses production of DNA sequences which encode HLPAAT and HLPAAT derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HLPAAT or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerases (Amersham, Chicago, Ill.), or combinations of polymerases and proofreading exonucleases such as those found in the ELONGASE amplification system (GIBCO/BRL, Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the AB CATALYST and 373 and 377 DNA sequencers (Perkin Elmer).

The nucleic acid sequences encoding HLPAAT may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer which is complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR software, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HLPAAT may be used in recombinant DNA molecules to direct expression of HLPAAT, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HLPAAT.

As will be understood by those of skill in the art, it may be advantageous to produce HLPAAT-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HLPAAT-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HLPAAT may be ligated to a heterologous sequence to encode a fusion protein. For example, to screen peptide libraries for inhibitors of HLPAAT activity, it may be useful to encode a chimeric HLPAAT protein that can be recognized by a commercially available antibody. A fusion protein may also be engineered to contain a cleavage site located between the HLPAAT encoding sequence and the heterologous protein sequence, so that HLPAAT may be cleaved and purified away from the heterologous moiety.

In another embodiment, sequences encoding HLPAAT may be synthesized, in whole or in part, using chemical methods well known in the art. (See, e.g., Caruthers, M. H. et al. (1980) Nucl. Acids Res. Symp. Ser. 7:215–223, and Horn, T. et al. (1980) Nucl. Acids Res. Symp. Ser. 7:225–232.) Alternatively, the protein itself may be produced using chemical methods to synthesize the amino acid sequence of HLPAAT, or a fragment thereof. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin Elmer). Additionally, the amino acid sequence of HLPAAT, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular Properties*, W H Freeman and Co., New York, N.Y.)

In order to express a biologically active HLPAAT, the nucleotide sequences encoding HLPAAT or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HLPAAT and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HLPAAT. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding HLPAAT which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the BLUESCRIPT phagemid (Stratagene, La Jolla, Calif.) or PSPORT1 plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HLPAAT, vectors based on SV40 or EBV may be used with an appropriate selectable marker.

In bacterial systems, a number of expression vectors may be selected depending upon the use intended for HLPAAT. For example, when large quantities of HLPAAT are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding HLPAAT may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) PGEX vectors (Amersham Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HLPAAT may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HLPAAT. For example, in one such system, *Autographa californica* nuclear polyhedrosis virus (AcNPV) is used as a vector to express foreign genes in *Spodoptera frugiperda* cells or in Trichoplusia larvae. The sequences encoding HLPAAT may be cloned into a non-essential region of the virus, such as the polyhedrin gene, and placed under control of the polyhedrin promoter. Successful insertion of sequences encoding HLPAAT will render the polyhedrin gene inactive and produce recombinant virus lacking coat protein. The recombinant viruses may then be used to infect, for example, *S. frugiperda* cells or Trichoplusia larvae in which HLPAAT may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HLPAAT may be ligated into an adenovirus transcription/translation complex consisting of the late promoter and tripartite leader sequence. Insertion in a non-essential E1 or E3 region of the viral genome may be used to obtain a viable virus which is capable of expressing HLPAAT in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HLPAAT. Such signals include the ATG initiation codon and adjacent sequences. In cases where sequences encoding HLPAAT and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HLPAAT can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G–418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, β glucuronidase and its substrate GUS, luciferase and its substrate luciferin may be used. Green fluorescent proteins (GFP) (Clontech, Palo Alto, Calif.) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HLPAAT is inserted within a marker gene sequence, transformed cells containing sequences encoding HLPAAT can be identified by the absence of marker gene function. Alternatively, a marker gene can be placed in tandem with a sequence encoding HLPAAT under the control of a single promoter. Expression of the marker gene in response to induction or selection usually indicates expression of the tandem gene as well.

Alternatively, host cells which contain the nucleic acid sequence encoding HLPAAT and express HLPAAT may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HLPAAT can be detected by DNA-DNA or DNA-RNA hybridization or amplification using probes or fragments or fragments of polynucleotides encoding HLPAAT. Nucleic acid amplification based assays involve the use of oligonucleotides or oligomers based on the sequences encoding HLPAAT to detect transformants containing DNA or RNA encoding HLPAAT.

A variety of protocols for detecting and measuring the expression of HLPAAT, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HLPAAT is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HLPAAT include oligolabeling, nick translation, end-labeling, or PCR amplification using a labeled nucleotide. Alternatively, the sequences encoding HLPAAT, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HLPAAT may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HLPAAT may be designed to contain signal sequences which direct secretion of HLPAAT through a prokaryotic or eukaryotic cell membrane. Other constructions may be used to join sequences encoding HLPAAT to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences, such as those specific for Factor XA or enterokinase (Invitrogen, San Diego, Calif.), between the purification domain and the HLPAAT encoding sequence may be used to facilitate purification. One such expression vector provides for expression of a fusion protein containing HLPAAT and a nucleic acid encoding 6 histidine residues preceding a thioredoxin or an enterokinase cleavage site. The histidine residues facilitate purification on immobilized metal ion affinity chromatography (IMIAC). (See, e.g., Porath, J. et al. (1992) Prot. Exp. Purif. 3:263–281.) The enterokinase cleavage site provides a means for purifying HLPAAT from the fusion protein. (See, e.g., Kroll, D. J. et al. (1993) DNA Cell Biol. 12:441–453.)

Fragments of HLPAAT may be produced not only by recombinant production, but also by direct peptide synthesis using solid-phase techniques. (See, e.g., Creighton, T. E. (1984) Protein: Structures and Molecular Properties, pp. 55–60, W. H. Freeman and Co., New York, N.Y.) Protein synthesis may be performed by manual techniques or by automation. Automated synthesis may be achieved, for example, using the Applied Biosystems 431A peptide synthesizer (Perkin Elmer). Various fragments of HLPAAT may be synthesized separately and then combined to produce the full length molecule.

Therapeutics

Chemical and structural homology exists between HLPAAT and lysophosphatidic acid acyltransferase from mouse (GI 2317725). In addition, HLPAAT is expressed in libraries from cancerous and immune system tissues. Therefore, HLPAAT appears to play a role in cancer and autoimmune disorders.

Therefore, in one embodiment, HLPAAT or a fragment or derivative thereof may be administered to a subject to treat or prevent a cancer. Such a cancer can include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HLPAAT or a fragment or derivative thereof may be administered to a subject to treat or prevent a cancer including, but not limited to, those described above.

In a further embodiment, a pharmaceutical composition comprising a substantially purified HLPAAT in conjunction with a suitable pharmaceutical carrier may be administered to a subject to treat or prevent a cancer including, but not limited to, those provided above.

In still another embodiment, an agonist which modulates the activity of HLPAAT may be administered to a subject to treat or prevent a cancer including, but not limited to, those listed above.

In a further embodiment, an antagonist of HLPAAT may be administered to a subject to treat or prevent an autoimmune disorder. Such a disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. In one aspect, an antibody which specifically binds HLPAAT may be used directly as an antagonist or indirectly as a targeting or delivery mechanism for bringing a pharmaceutical agent to cells or tissue which express HLPAAT.

In an additional embodiment, a vector expressing the complement of the polynucleotide encoding HLPAAT may be administered to a subject to treat or prevent an autoimmune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HLPAAT may be produced using methods which are generally known in the art. In particular, purified HLPAAT may be used to produce antibodies or to screen libraries of pharmaceutical agents to identify those which specifically bind HLPAAT. Antibodies to HLPAAT may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HLPAAT or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HLPAAT have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HLPAAT amino acids may be fused with those of another protein, such as KLH, and antibodies to the chimeric molecule may be produced.

Monoclonal antibodies to HLPAAT may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HLPAAT-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86:3833–3837; and Winter, G. et al. (1991) Nature 349:293–299.)

Antibody fragments which contain specific binding sites for HLPAAT may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HLPAAT and its specific antibody. A two-site, monoclonal-based immunoassay utilizing monoclonal antibodies reactive to two non-interfering HLPAAT epitopes is preferred, but a competitive binding assay may also be employed. (Maddox, supra.)

In another embodiment of the invention, the polynucleotides encoding HLPAAT, or any fragment or complement thereof, may be used for therapeutic purposes. In one aspect, the complement of the polynucleotide encoding HLPAAT may be used in situations in which it would be desirable to block the transcription of the mRNA. In particular, cells may be transformed with sequences complementary to polynucleotides encoding HLPAAT. Thus, complementary molecules or fragments may be used to modulate HLPAAT activity, or to achieve regulation of gene function. Such technology is now well known in the art, and sense or antisense oligonucleotides or larger fragments can be designed from various locations along the coding or control regions of sequences encoding HLPAAT.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HLPAAT. (See, e.g., Sambrook, supra; and Ausubel, supra.)

Genes encoding HLPAAT can be turned off by transforming a cell or tissue with expression vectors which express high levels of a polynucleotide, or fragment thereof, encoding HLPAAT. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HLPAAT. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HLPAAT.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HLPAAT. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HLPAAT, antibodies to HLPAAT, and mimetics, agonists, antagonists, or inhibitors of HLPAAT. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Science* (Maack Publishing Co., Easton, Pa).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HLPAAT, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HLPAAT or fragments thereof, antibodies of HLPAAT, and agonists, antagonists or inhibitors of HLPAAT, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HLPAAT may be used for the diagnosis of disorders characterized by expression of HLPAAT, or in assays to monitor patients being treated with HLPAAT or agonists, antagonists, or inhibitors of HLPAAT. Antibodies useful for diagnostic purposes may be prepared in the same manner as described above for therapeutics. Diagnostic assays for HLPAAT include methods which utilize the antibody and a label to detect HLPAAT in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HLPAAT, including ELISAs, RIAs, and FACS, are known in the art and provide a basis for diagnosing altered or abnormal levels of HLPAAT expression. Normal or standard values for HLPAAT expression are established by combining body fluids or cell extracts taken from normal mammalian subjects, preferably human, with antibody to HLPAAT under conditions suitable for complex formation The amount of standard complex formation may be quantitated by various methods, preferably by photometric means. Quantities of HLPAAT expressed in subject, control, and disease samples from biopsied tissues are compared with the standard values. Deviation between standard and subject values establishes the parameters for diagnosing disease.

In another embodiment of the invention, the polynucleotides encoding HLPAAT may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HLPAAT may be correlated with disease. The diagnostic assay may be used to determine absence, presence, and excess expression of HLPAAT, and to monitor regulation of HLPAAT levels during therapeutic intervention.

In one aspect, hybridization with PCR probes which are capable of detecting polynucleotide sequences, including genomic sequences, encoding HLPAAT or closely related molecules may be used to identify nucleic acid sequences which encode HLPAAT. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HLPAAT, alleles, or related sequences.

Probes may also be used for the detection of related sequences, and should preferably have at least 50% sequence identity to any of the HLPAAT encoding sequences. The hybridization probes of the subject invention may be DNA or RNA and may be derived from the sequence of SEQ ID NO:2 or from genomic sequences including promoters, enhancers, and introns of the HLPAAT gene.

Means for producing specific hybridization probes for DNAs encoding HLPAAT include the cloning of polynucleotide sequences encoding HLPAAT or HLPAAT derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HLPAAT may be used for the diagnosis of a disorder associated with expression of HLPAAT. Examples of such a disorder include, but are not limited to, cancers, including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, and autoimmune disorders, including AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding HLPAAT may be used in Southern or northern analysis, dot blot, or other membrane-based technologies; in PCR technologies; in dipstick, pin, and ELISA assays; and in microarrays utilizing fluids or tissues from patients to detect altered HLPAAT expression. Such qualitative or quantitative methods are well known in the art.

In a particular aspect, the nucleotide sequences encoding HLPAAT may be useful in assays that detect the presence of associated disorders, particularly those mentioned above. The nucleotide sequences encoding HLPAAT may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HLPAAT in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HLPAAT, a normal or standard profile for expression is established. This may be accomplished by combining body fluids or cell extracts taken from normal subjects, either animal or human, with a sequence, or a fragment thereof, encoding HLPAAT, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HLPAAT may involve the use of PCR. These oligomers may be chemically synthesized, generated enzymatically, or produced in vitro. Oligomers will preferably contain a fragment of a polynucleotide encoding HLPAAT, or a fragment of a polynucleotide complementary to the polynucleotide encoding HLPAAT, and will be employed under optimized conditions for identification of a specific gene or condition. Oligomers may also be employed under less stringent conditions for detection or quantitation of closely related DNA or RNA sequences.

Methods which may also be used to quantitate the expression of HLPAAT include radiolabeling or biotinylating nucleotides, coamplification of a control nucleic acid, and interpolating results from standard curves. (See, e.g., Melby, P.C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO095/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HLPAAT may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HLPAAT on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HLPAAT, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HLPAAT and the agent being tested may be measured.

Another technique for drug screening provides for high throughput screening of compounds having suitable binding affinity to the protein of interest. (See, e.g., Geysen, et al. (1984) PCT application WO084/03564.) In this method, large numbers of different small test compounds are synthesized on a solid substrate, such as plastic pins or some other surface. The test compounds are reacted with HLPAAT, or fragments thereof, and washed. Bound HLPAAT is then detected by methods well known in the art. Purified HLPAAT can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HLPAAT specifically compete with a test compound for binding HLPAAT. In this manner, antibodies can be used to detect the presence of any peptide which shares one or more antigenic determinants with HLPAAT.

In additional embodiments, the nucleotide sequences which encode HLPAAT may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. BEPINOT01 cDNA Library Construction

The BEPINOT01 cDNA library was constructed from a microscopically normal bronchial epithelium (NHBE) primary cell line derived from a 54-year-old Caucasian male.

The frozen tissue was homogenized and lysed using a Brinkmann POLYTRON homogenizer PT-3000 (Brinkmann Instruments, Westbury, N.J.). The lysate was centrifuged over a 5.7 M CsCl cushion using an Beckman SW28 rotor in a Beckman L8-70M ultracentrifuge (Beckman Instruments) for 18 hours at 25,000 rpm at ambient temperature. The RNA was extracted with acid phenol chloroform pH 8.0, precipitated using 0.3 M sodium acetate and 2.5 volumes of ethanol, resuspended in DEPC-treated water, and DNase treated at 37° C. RNA extraction and precipitation were repeated as before. The RNA was then isolated using the Qiagen OLIGOTEX kit (QIAGEN, Inc., Chatsworth, Calif.) and used to construct the cDNA library.

The RNA was handled according to the recommended protocols in the SUPERSCRIPT plasmid system (Catalog #18248-013, Gibco/BRL, Gaithersburg, Md.). cDNAs were fractionated on a SEPHAROSE CL4B column (Pharmacia), and those cDNAs exceeding 400 bp were ligated into PSPORT1. The plasmid PSPORT1 was subsequently transformed into DH12S competent cells (Gibco/BRL).

II. Isolation and Sequencing of cDNA Clones

Plasmid DNA was released from the cells and purified using the REAL PREP 96-well plasmid purification kit (QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton MICROLAB 2200 (Hamilton, Reno, Nev.) in combination with Peltier thermal cyclers (PTC200 from M J Research, Watertown, Mass.) and Applied Biosystems 377 DNA sequencing systems; and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the BLOCK 2 bioanalysis program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1% to 2% error, and, with a product score of 70, the match will be exact Homologous molecules are usually identified by selecting those which show product scores between 15 and 40, although lower scores may identify related molecules.

The results of northern analysis are reported as a list of libraries in which the transcript encoding HLPAAT occurs. Abundance and percent abundance are also reported. Abundance directly reflects the number of times a particular transcript is represented in a cDNA library, and percent abundance is abundance divided by the total number of sequences examined in the cDNA library.

V. Extension of HLPAAT Encoding Polynucleotides

The nucleic acid sequence of Incyte Clone 2057904 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 primer analysis software (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier thermal cycler (PTC200; M. J. Research, Watertown, Mass.), beginning with 40 pmol of each primer and the recommended concentrations of all other components of the kit, with the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat steps 4 through 6 for an additional 15 cycles
Step 8 94° C. for 15 sec
Step 9 65° C. for 1 min
Step 10 68° C. for 7:15 min
Step 11 Repeat steps 8 through 10 for an additional 12 cycles
Step 12 72° C. for 8 min
Step 13 4° C. (and holding)

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK DNA purification kit (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2×carb). The following day, several colonies were randomly picked from each plate and cultured in 150 µl of liquid LB/2×Carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

Step 1 94° C. for 60 sec
Step 2 94° C. for 20 sec
Step 3 55° C. for 30 sec
Step 4 72° C. for 90 sec
Step 5 Repeat steps 2 through 4 for an additional 29 cycles
Step 6 72° C. for 180 sec
Step 7 4° C. (and holding)

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 primer analysis software (National Biosciences) and labeled by combining 50 pmol of each oligomer, 250 µCi of [$\gamma$-$^{32}$P]adenosine triphosphate (Amersham, Chicago, Ill.), and T4 polynucleotide kinase (DuPont NEN®, Boston, Mass.). The labeled oligonucleotides are substantially purified using a SEPHADEX G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7 percent agarose gel and transferred to nylon membranes NYTRAN PLUS membrane, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT ART autoradiography film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HLPAAT-encoding sequences, or any parts thereof, are used to detect, decrease, or inhibit expression of naturally occurring HLPAAT. Although use of oligonucleotides comprising from about 15 to 30 base pairs is described, essentially the same procedure is used with smaller or with larger sequence fragments. Appropriate oligonucleotides are designed using OLIGO 4.06 primer analysis software and the coding sequence of HLPAAT. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HLPAAT-encoding transcript.

IX. Expression of HLPAAT

Expression of HLPAAT is accomplished by subcloning the cDNA into an appropriate vector and transforming the vector into host cells. This vector contains an appropriate promoter, e.g., β-galactosidase, upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HLPAAT into bacterial growth media which can be used directly in the following assay for activity.

X. Demonstration of HLPAAT Activity

HLPAAT catalyzes the transfer of an acyl group from a donor such as acyl-CoA to LPA. Transfer of the acyl group releases free CoA, which can be reacted with the thiol reagent, 5,5'-dithiobis(2-nitrobenzoic acid) (DTNB). The product of the reaction between DTNB and free CoA absorbs at 413 nm. Samples containing HLPAAT are incubated with 1 mM DTNB, 50 μm LPA, and 50 μm acyl-CoA in 100 mM Tris-HCl, pH 7.4. The reaction is initiated by addition of acyl-CoA, and allowed to reach equilibrium. The change in absorbance at 413 nm is measured using a spectrophotometer, and is proportional to the activity of HLPAAT in the sample.

XI. Production of HLPAAT Specific Antibodies

HLPAAT substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the HLPAAT amino acid sequence is analyzed using LASERGENE software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems 43 1A Peptide synthesizer using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HLPAAT Using Specific Antibodies

Naturally occurring or recombinant HLPAAT is substantially purified by immunoaffinity chromatography using antibodies specific for HLPAAT. An immunoaffinity column is constructed by covalently coupling anti-HLPAAT antibody to an activated chromatographic resin, such as CNBr-activated SEPHAROSE (Pharmacia & Upjohn). After the coupling, the resin is blocked and washed according to the manufacturer's instructions.

Media containing HLPAAT are passed over the immunoaffinity column, and the column is washed under conditions that allow the preferential absorbance of HLPAAT (e.g., high ionic strength buffers in the presence of detergent). The column is eluted under conditions that disrupt antibody/HLPAAT binding (e.g., a buffer of pH 2 to pH 3, or a high concentration of a chaotrope, such as urea or thiocyanate ion), and HLPAAT is collected.

XIII. Identification of Molecules Which Interact with HLPAAT

HLPAAT, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HLPAAT, washed, and any wells with labeled HLPAAT complex are assayed. Data obtained using different concentrations of HLPAAT are used to calculate values for the number, affinity, and association of HLPAAT with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified polypeptide comprising the amino acid sequence of SEQ ID No:1.

2. A composition comprising the polypeptide of claim 1.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 334 amino acids
      (B) TYPE: amino acid
      (C) STRANDEDNESS: single
      (D) TOPOLOGY: linear (vii) IMMEDIATE SOURCE:
      (A) LIBRARY: BEPINOT01
      (B) CLONE: 2057904

(xi) SEQUENCE DESCRIPTION: SEQ ID NO:1:

```
Met Glu Thr Ile Met Asp Asp Glu Val Thr Lys Arg Phe Ser Ala Glu
 1               5                  10                  15

Glu Leu Glu Ser Trp Asn Leu Leu Ser Arg Thr Asn Tyr Asn Phe Gln
             20                  25                  30

Tyr Ile Ser Leu Arg Leu Thr Val Leu Trp Gly Leu Gly Val Leu Ile
         35                  40                  45

Arg Tyr Cys Phe Leu Leu Pro Leu Arg Ile Ala Leu Ala Phe Thr Gly
 50                  55                  60

Ile Ser Leu Leu Val Val Gly Thr Thr Val Val Gly Tyr Leu Pro Asn
 65                  70                  75                  80

Gly Arg Phe Lys Glu Phe Met Ser Lys His Val His Leu Met Cys Tyr
                 85                  90                  95

Arg Ile Cys Val Arg Ala Leu Thr Ala Ile Ile Thr Tyr His Asp Arg
                100                 105                 110

Glu Asn Arg Pro Arg Asn Gly Gly Ile Cys Val Ala Asn His Thr Ser
                115                 120                 125

Pro Ile Asp Val Ile Ile Leu Ala Ser Asp Gly Tyr Tyr Ala Met Val
        130                 135                 140

Gly Gln Val His Gly Gly Leu Met Gly Val Ile Gln Arg Ala Met Val
145                 150                 155                 160

Lys Ala Cys Pro His Val Trp Phe Glu Arg Ser Glu Val Lys Asp Arg
                165                 170                 175

His Leu Val Ala Lys Arg Leu Thr Glu His Val Gln Asp Lys Ser Lys
                180                 185                 190

Leu Pro Ile Leu Ile Phe Pro Glu Gly Thr Cys Ile Asn Asn Thr Ser
            195                 200                 205

Val Met Met Phe Lys Lys Gly Ser Phe Glu Ile Gly Ala Thr Val Tyr
        210                 215                 220

Pro Val Ala Ile Lys Tyr Asp Pro Gln Phe Gly Asp Ala Phe Trp Asn
225                 230                 235                 240

Ser Ser Lys Tyr Gly Met Val Thr Tyr Leu Leu Arg Met Met Thr Ser
                245                 250                 255

Trp Ala Ile Val Cys Ser Val Trp Tyr Leu Pro Pro Met Thr Arg Glu
                260                 265                 270

Ala Asp Glu Asp Ala Val Gln Phe Ala Asn Arg Val Lys Ser Ala Ile
            275                 280                 285

Ala Arg Gln Gly Gly Leu Val Asp Leu Leu Trp Asp Gly Gly Leu Lys
        290                 295                 300

Arg Glu Lys Val Lys Asp Thr Phe Lys Glu Glu Gln Gln Lys Leu Tyr
```

```
305                 310                 315                 320
Ser Lys Met Ile Val Gly Asn His Lys Asp Arg Ser Arg Ser
                325                 330
```

(2) INFORMATION FOR SEQ ID NO:2:

(i) SEQUENCE CHARACTERISTICS:
        (A) LENGTH: 3192 base pairs
        (B) TYPE: nucleic acid
        (C) STRANDEDNESS: single
        (D) TOPOLOGY: linear (vii) IMMEDIATE SOURCE:
        (A) LIBRARY: BEPINOT01
        (B) CLONE: 2057904

(xi) SEQUENCE DESCRIPTION: SEQ ID NO:2:

```
CCCACGCGTC CGGCGGTCGC CGCGGGATTT GGAGCTGCCT AGCCTCGCGG TCGCTTTGGC    60
AGCATGTAAG CAGCTGTTTG CCAAGAACCC AGGTCACTGC TAAGAAAGGG TGCCTTCGGG   120
AGAAGAGTGT CCAGAGGATA CCAATGCCAG ATGCATCTGG AGTTACACTC AGCACTCGCA   180
GTATGAGACA TTGTGTGCCA GCATCTCTTT CCTTCTGGCA AAGACTGTAG CTCTCCAGGT   240
AGGAGGATCC TGGAAGCTGT GAGCACCAGG AGCCTTGCCA GAGGAGGATG GGCCAGATA    300
TGAACTCTCT ACCATGAACA TGGTTCTCGG CTTATGAAGG AATTTTAAGT AAAACAGTTA   360
TTTAATTTCC ACATATTCAA GTCAAAAGCC TTCTGTGTGA AGTGCCAGTG ATTACCCCTC   420
CACAGGAGTT ATCAGGATTT TTCTGGCACC AAGTTTAATT CTTCTTCGTA CTTCTGGTAG   480
TGACAGATCT GCAGGGCAGA TTTATCTGTT GAATGCTCTT GGGCAGGAAA ACCATGTAAA   540
ACCTCTGGAA GCAGCATCAG GACAGCAGAG CAGAGCCCCC GTCCTCACTG CTCACTTGCA   600
CAGAAACTCC ATCTGGACTC GGATGCTTTT ACTGAAGACC CATCTAGCTT CAATCATCTT   660
TAGAGTCCAT CCATTCTGGA GAGACCTGGC GTTTGCAGTT GCCTCCTGTG GCCGTGTTTT   720
TCTGTCATTC TGTTCCCAGG CCTTCTATTC AGGCGGTTGA AGGGTGTGGA CTTTGGAATG   780
GGGTTTGCTG TTCTTCGGGA ACTTGCTTCC TTTCCCTGGC TGGTGCTGTC AGGAAGGACC   840
ATCTGAAGGC TGCAATTTGT TCTTAGGGAG GCAGGTGCTG GCCTGGCCTG GATCTTCCAC   900
CATGTTCCTG TTGCTGCCTT TTGATAGCCT GATTGTCAAC CTTCTGGGCA TCTCCCTGAC   960
TGTCCTCTTC ACCCTCCTTC TCGTTTTCAT CATAGTGCCA GCCATTTTTG GAGTCTCCTT  1020
TGGTATCCGC AAACTCTACA TGAAAAGTCT GTTAAAAATC TTTGCGTGGG CTACCTTGAG  1080
AATGGAGCGA GGAGCCAAGG AGAAGAACCA CCAGCTTTAC AAGCCCTACA CCAACGGAAT  1140
CATTGCAAAG GATCCCACTT CACTAGAAGA AGAGATCAAA GAGATTCGTC GAAGTGGTAG  1200
TAGTAAGGCT CTGGACAACA CTCCAGAGTT CGAGCTCTCT GACATTTTCT ACTTTTGCCG  1260
GAAAGGAATG GAGACCATTA TGGATGATGA GGTGACAAAG AGATTCTCAG CAGAAGAACT  1320
GGAGTCCTGG AACCTGCTGA GCAGAACCAA TTATAACTTC CAGTACATCA GCCTTCGGCT  1380
CACGGTCCTG TGGGGTTAG GAGTGCTGAT TCGGTACTGC TTTCTGCTGC CGCTCAGGAT   1440
AGCACTGGCT TTCACAGGGA TTAGCCTTCT GGTGGTGGGC ACAACTGTGG TGGGATACTT  1500
GCCAAATGGG AGGTTTAAGG AGTTCATGAG TAAACATGTT CACTTAATGT GTTACCGGAT  1560
CTGCGTGCGA GCGCTGACAG CCATCATCAC CTACCATGAC AGGGAAAACA GACCAAGAAA  1620
TGGTGGCATC TGTGTGGCCA ATCATACCTC ACCGATCGAT GTGATCATCT TGGCCAGCGA  1680
TGGCTATTAT GCCATGGTGG GTCAAGTGCA CGGGGGACTC ATGGGTGTGA TTCAGAGAGC  1740
CATGGTGAAG GCCTGCCCAC ACGTCTGGTT TGAGCGCTCG GAAGTGAAGG ATCGCCACCT  1800
```

```
GGTGGCTAAG AGACTGACTG AACATGTGCA AGATAAAAGC AAGCTGCCTA TCCTCATCTT    1860

CCCAGAAGGA ACCTGCATCA ATAATACATC GGTGATGATG TTCAAAAAGG GAAGTTTTGA    1920

AATTGGAGCC ACAGTTTACC CTGTTGCTAT CAAGTATGAC CCTCAATTTG GCGATGCCTT    1980

CTGGAACAGC AGCAAATACG GGATGGTGAC GTACCTGCTG CGAATGATGA CCAGCTGGGC    2040

CATTGTCTGC AGCGTGTGGT ACCTGCCTCC CATGACTAGA GAGGCAGATG AAGATGCTGT    2100

CCAGTTTGCG AATAGGGTGA AATCTGCCAT TGCCAGGCAG GGAGGACTTG TGGACCTGCT    2160

GTGGGATGGG GGCCTGAAGA GGGAGAAGGT GAAGGACACG TTCAAGGAGG AGCAGCAGAA    2220

GCTGTACAGC AAGATGATCG TGGGGAACCA CAAGGACAGG AGCCGCTCCT GAGCCTGCCT    2280

CCAGCTGGCT GGGGCCACCG TGCGGGGTGC AACGGGCTC AGAGCTGGAG TTGCCGCCGC    2340

CGCCCCCACT GCTGTGTCCT TTCCAGACTC CAGGGCTCCC CGGGCTGCTC TGGATCCCAG    2400

GACTCCGGCT TTCGCCGAGC CGCAGCGGGA TCCCTGTGCA CCCGGCGCAG CTACCCTTGG    2460

TGGTCTAAAC GGATGCTGCT GGGTGTTGCG ACCCAGGACG AGATGCCTTG TTTCTTTTAC    2520

AATAAGTCGT TGGAGGAATG CCATTAAAGT GAACTCCCCA CCTTTGCACG CTGTGCGGGC    2580

TGAGTGGTTG GGGAGATGTG GCCATGGTCT TGTGCTAGAG ATGGCGGTAC AAGAGTCTGT    2640

TATGCAAGCC CGTGTGCCAG GGATGTGCTG GGGGCGGCCA CCCGCTCTCC AGGAAAGGCA    2700

CAGCTGAGGC ACTGTGGCTG GCTTCGGCCT CAACATCGCC CCCAGCCTTG GAGCTCTGCA    2760

GACATGATAG GAAGGAAACT GTCATCTGCA GGGGCTTTCA GCAAAATGAA GGGTTAGATT    2820

TTTATGCTGC TGCTGATGGG GTTACTAAAG GGAGGGGAAG AGGCCAGGTG GGCCGCTGAC    2880

TGGGCCATGG GGAGAACGTG TGTTCGTACT CCAGGCTAAC CCTGAACTCC CCATGTGATG    2940

CGCGCTTTGT TGAATGTGTG TCTCGGTTTC CCCATCTGTA ATATGAGTCG GGGGGAATGG    3000

TGGTGATTCC TACCTCACAG GGCTGTTGTG GGGATTAAAG TGCTGCGGGT GAGTGAAGGA    3060

CACATCACGT TCAGTGTTTC AAGTACAGGC CCACAAAACG GGGCACGGCA GGCCTGAGCT    3120

CAGAGCTGCT GCACTGGGCT TTGGATTTGT TCTTGTGAGT AAATAAAACT GGCTGGTGAA    3180

TGAAAAAAAA AA                                                      3192
```

(2) INFORMATION FOR SEQ ID NO:3:

(i) SEQUENCE CHARACTERISTICS:
        (A) LENGTH: 294 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 2317725

(xi) SEQUENCE DESCRIPTION: SEQ ID NO:3:

```
Met Glu Thr Ile Met Asp Asp Glu Val Thr Lys Arg Thr Ser Ala Glu
 1               5                  10                  15

Glu Leu Glu Ser Trp Asn Leu Leu Ser Arg Thr Asn Tyr Asn Phe Gln
            20                  25                  30

Tyr Ile Ser Leu Arg Leu Thr Ile Leu Trp Gly Leu Gly Val Leu Ile
        35                  40                  45

Arg Tyr Cys Phe Leu Leu Pro Leu Arg Ile Ala Leu Ala Phe Thr Gly
    50                  55                  60

Ile Gly Leu Leu Val Val Gly Thr Thr Met Val Gly Tyr Leu Pro Asn
65                  70                  75                  80

Gly Arg Phe Lys Glu Phe Leu Ser Lys His Val His Leu Met Cys Tyr
                85                  90                  95
```

```
Arg Ile Cys Val Arg Ala Leu Thr Ala Ile Ile Thr Tyr His Asn Arg
            100                 105                 110

Lys Asn Arg Pro Arg Asn Gly Gly Ile Cys Val Ala Asn His Thr Ser
            115                 120                 125

Arg Ile Asp Val Ile Ile Phe Ala Ser Asp Gly Tyr Tyr Ala Met Val
            130                 135                 140

Gly Gln Val His Gly Gly Leu Met Gly Val Ile Gln Arg Ala Met Val
145                 150                 155                 160

Lys Ala Cys Pro His Val Trp Phe Glu Arg Ser Glu Val Lys Asp Arg
            165                 170                 175

His Leu Val Ala Lys Arg Leu Thr Glu His Val Gln Asp Lys Ser Lys
            180                 185                 190

Leu Pro Ile Leu Ile Phe Pro Glu Gly Thr Cys Ile Asn Asn Thr Ser
            195                 200                 205

Val Met Met Phe Lys Lys Gly Ser Phe Glu Ile Gly Ala Thr Val Tyr
            210                 215                 220

Pro Val Ala Ile Lys Tyr Asp Pro Gln Phe Gly Asp Ala Phe Trp Asn
225                 230                 235                 240

Ser Ser Lys Tyr Gly Met Val Thr Tyr Leu Leu Arg Met Met Thr Ser
            245                 250                 255

Trp Ala Ile Val Cys Ser Val Trp Tyr Leu Pro Pro Met Thr Arg Glu
            260                 265                 270

Lys Asp Glu Asp Ala Val Gln Phe Ala Asn Arg Val Lys Ser Ala Ile
            275                 280                 285

Ala Arg Gln Glu Asp Trp
    290
```